United States Patent [19]

Yamakawa et al.

[11] Patent Number: 5,521,318

[45] Date of Patent: May 28, 1996

[54] BENZOTRIAZOLYLACETYL COMPOUND

[75] Inventors: Katsuyoshi Yamakawa; Tadahisa Sato; Koichi Hanaki, all of Minami-ashigara, Japan

[73] Assignee: Fuji Photo Film Co., Ltd., Kanagawa-ken, Japan

[21] Appl. No.: 426,897

[22] Filed: Apr. 21, 1995

[30] Foreign Application Priority Data

Apr. 27, 1994 [JP] Japan .................................. 6-110141

[51] Int. Cl.$^6$ ...................... C07D 417/14; C07D 417/04; C07D 403/14; C07D 403/10
[52] U.S. Cl. ........................ 548/261; 548/159; 548/259
[58] Field of Search .................................. 548/261, 159, 548/259

[56] References Cited

U.S. PATENT DOCUMENTS

| | | |
|---|---|---|
| 4,095,984 | 6/1978 | Sueyoshi et al. . |
| 4,121,934 | 10/1978 | Yagihara et al. ............................ 96/22 |
| 4,230,851 | 10/1980 | Renner et al. . |
| 4,477,563 | 10/1984 | Ichijima et al. . |
| 5,213,958 | 5/1993 | Motoki et al. . |

*Primary Examiner*—Patricia L. Morris
*Attorney, Agent, or Firm*—Birch, Stewart, Kolasch & Birch

[57] ABSTRACT

There is disclosed a compound represented by formula (I):

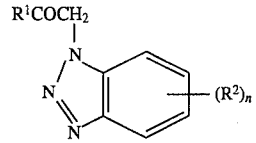

wherein $R^1$ represents a tert-butyl group, a phenyl group having an alkoxy group with 1 to 18 carbon atoms in the paraposition, or an indoline-1-yl group; $R^2$ represents a group substitutable on the benzene ring; and n is an integer of 0 to 4, provided that when $R^1$ represents a tert-butyl group, n is not 0. The compound may be used as a synthesis intermediate from which a yellow coupler can be synthesized in a simple manner. Using the compound, a yellow coupler can be readily produced on an industrial scale with the short process.

6 Claims, No Drawings

BENZOTRIAZOLYLACETYL COMPOUND

FIELD OF THE INVENTION

The present invention relates to a novel substituted acetyl compound that is used as a synthetic intermediate, for example, in the production of a yellow coupler used as a recording material, such as a silver halide color photographic material, and in the production of an intermediate for medicines.

BACKGROUND OF THE INVENTION

As a yellow coupler used in color photographic materials, two-equivalent couplers having a substituted benzotriazolyl group in the coupling site are known (see, for example, U.S. Pat. Nos. 4,095,984, 4,477,563, and 5,213,958). As a method for synthesizing this yellow coupler, Scheme 1, as shown below, is known. That is, generally a β-ketoester compound 1 is used as a key intermediate, to be reacted with an aniline compound, to obtain a β-ketoanilide compound 2, which is then halogenated (to obtain 3), followed by a substitution reaction (to obtain 4).

Sheme 1

$R^3COCl \longrightarrow R^3COCH_2CO_2C_2H_5 \longrightarrow$
$$\qquad\qquad\qquad 1$$

$R^3COCH_2CONHAr \longrightarrow R^3COCHCONHAr \longrightarrow$
$$\qquad\qquad\qquad\qquad\qquad\qquad\quad |$$
$$\qquad\qquad\qquad\qquad\qquad\quad\ \ X$$
$$\quad 2 \qquad\qquad\qquad\qquad 3$$

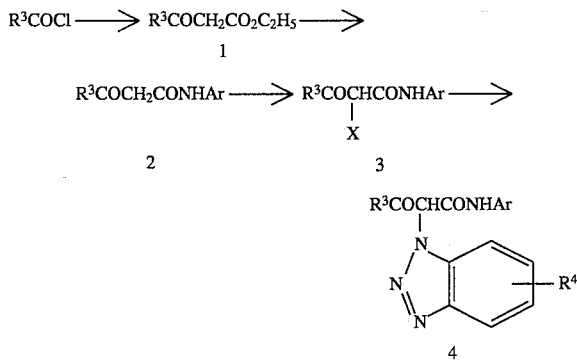

wherein $R^3$ represents an alkyl group, an aryl group, or a heterocyclic residue, Ar represents an aryl group, X represents a halogen atom, and $R^4$ represents a substituent substitutable on the benzene ring.

However, for example, this method requires a high temperature in the step for converting a β-ketoester compound to a β-ketoanilide compound; partially reducing dehalogenation takes place in the step for introducing a coupling split-off group (a coupling releasing group); and it is required to use the coupling split-off group in excess. Therefore, it has been attempted to improve this method (see U.S. Pat. No. 4,230,851), but a satisfactory method has not yet been developed.

SUMMARY OF THE INVENTION

The object of the present invention is to overcome these difficulties of the conventional synthesis of a yellow coupler, and to provide a novel synthetic intermediate useful in readily synthesizing a yellow coupler used in a silver halide color photographic material.

Other and further objects, features, and advantages of the invention will appear more fully from the following description.

DETAILED DESCRIPTION OF THE INVENTION

The present inventors have keenly studied to overcome the problems in the conventional production of a yellow coupler. As a result, we have found that a compound represented by the formula (I):

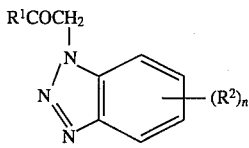

wherein $R^1$ represents a tert-butyl group, a phenyl group having an alkoxy group with 1 to 18 carbon atoms in the paraposition, or an indoline-1-yl group; $R^2$ represents a group substitutable on the benzene ring; and n is an integer of 0 to 4, provided that when $R^1$ represents a tert-butyl group, n is not 0, is suitable for the above object and can be a useful synthetic intermediate for the synthesis of a yellow coupler, leading to completion of the present invention.

Now the compound of the present invention will be described in detail.

$R^1$ represents a tert-butyl group, a phenyl group having an alkoxy group with 1 to 18 carbon atoms (e.g., methoxy, ethoxy, hexadecyloxy, and octadecyloxy) in the paraposition, or an indoline-1-yl group.

$R^2$ represents a group substitutable on the benzene ring, and examples include a halogen atom (e.g., fluorine, chlorine, bromine, and iodine atom), a cyano group, a nitro group, an alkoxy group having 1 to 20 carbon atoms (e.g., methoxy, butoxy, and octadecyloxy); an alkyl group having 1 to 20 carbon atoms, preferably 1 to 8 carbon atoms (e.g., methyl, ethyl, and butyl); an aryl group having 6 to 20 carbon atoms, preferably 6 to 10 carbon atoms (e.g., phenyl and naphthyl); an aryloxy group having 6 to 20 carbon atoms, preferably 6 to 10 carbon atoms (e.g., phenoxy and naphthyloxy); an aryloxycarbonyl group having 7 to 20 carbon atoms, preferably 7 to 11 carbon atoms (e.g., phenoxycarbonyl); an acylamino group having 1 to 20 carbon atoms, preferably 1 to 8 carbon atoms (e.g., formylamino, acetylamino, and octanoylamino); a sulfonamide group having 1 to 20 carbon atoms, preferably 1 to 8 carbon atoms (e.g., methanesulfonamide and p-toluenesulfonamide); a group represented by the formula (II), or a group represented by $—CO_2R^6$:

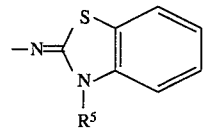

wherein $R^5$ represents an alkyl group having 1 to 20 carbon atoms, preferably 1 to 8 carbon atoms (e.g., methyl and ethyl).

$R^6$ represents an aryl group having 6 to 20 carbon atoms, preferably 6 to 10 carbon atoms (e.g., phenyl and naphthyl), or an alkyl group having 1 to 20 carbon atoms, preferably 1 to 8 carbon atoms (e.g., methyl and ethyl), which alkyl group may further be substituted by an alkoxycarbonyl group having 2 to 20 carbon atoms, preferably 2 to 8 carbon atoms (e.g., methoxycarbonyl, ethoxycarbonyl, and 3-methylbutoxycarbonyl).

Preferably $R^2$ represents an acylamino group having 1 to 8 carbon atoms, a group represented by formula (II) or a group represented by $—CO_2R^6$.

More preferably $R^2$ represents an acylamino group having 1 to 8 carbon atoms, a group represented by formula (II) (provided that $R^5$ represents a methyl group), or a group represented by —$CO_2R^6$ (provided that $R^6$ represents a phenyl group or a 3-methylbutoxycarbonylmethyl group). n is an integer of 0 to 4, with preference given to 0 or 2, provided that when $R^1$ represents a tert-butyl group, preferably n is 1.

The method for the production of the compound of the present invention will now be described.

The compound of the present invention can be obtained in good yield by reacting an α-haloacetyl compound with benzotriazoles under basic conditions as illustrated below. The molar ratio of the reaction of the α-haloacetyl compound with the benzotriazoles is generally from 1:5 to 5:1, preferably from 1:2 to 2:1.

Scheme 2

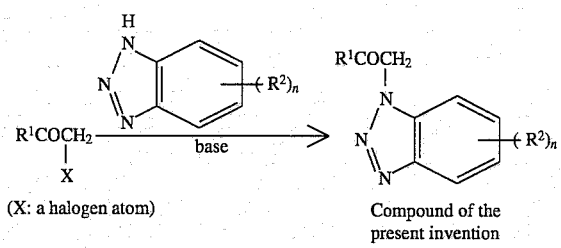

(X: a halogen atom)   Compound of the present invention wherein $R^1$, $R^2$ and n have the same meanings as defined above, and X represents a halogen atom.

As the base used in this reaction, an inorganic base, such as sodium hydride, potassium tert-butoxide, sodium carbonate, potassium carbonate, sodium methoxide, sodium ethoxide, sodium hydroxide, and potassium hydroxide; or an organic base, such as 1,8-diazabicyclo[5.4.0]-7-undecene (DBU), 1,5-diazabicyclo[4.3.0]-5-nonene (DBN), N,N-diisopropylethylamine, and triethylamine, can be used. The amount of the base to be used is not particularly restricted, and generally the amount of the base to be used is 0.5 to 2 equivalents, preferably 0.8 to 1.2 equivalents, based on the benzotriazoles. As the reaction solvent, ether, tetrahydrofuran (THF), dioxane, acetonitrile, N,N-dimethylformamide (DMF), N,N-dimethylacetamide (DMAc), 1,3-dimethyl-2-imidazolidone (DMI), 1-methyl-2-pyrrolidone (NMP), and the like can be used. The reaction temperature is 0° to 140° C., preferably 10° to 100° C. There is no restriction on the reaction time, and generally the reaction time is 0.5 to 10 hours, preferably 1 to 5 hours.

The compound of the present invention may be used in synthesizing a photographic yellow coupler as shown by the following Scheme:

Scheme 3

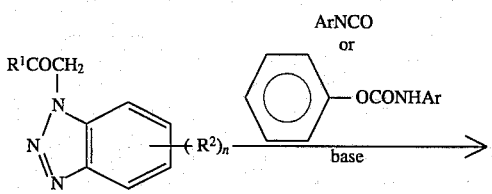

-continued
Scheme 3

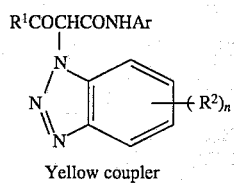

Yellow coupler wherein $R^1$, $R^2$ and n have the same meanings as defined above, and Ar represents an aromatic group.

When 1 mol of the compound of the present invention is reacted with 0.5 to 2 mol, preferably 0.8 to 1.2 mol, of an isocyanate compound or its precursor, a phenylurethane compound, in the presence of a base, the compound of the present invention is converted into a yellow coupler in a good yield. The isocyanate compound can be readily synthesized from a corresponding aniline derivative and a phosgene. The phenylurethane compound can be readily synthesized from a corresponding aniline derivative and a phenyl chlorocarbonate.

As the base to be used, for example, LDA (lithium diisopropylamide), sodium hydride, potassium tert-butoxide, and sodium methoxide can be mentioned.

The amount of the base to be used is 0.9 to 5 mol, preferably 1 to 3 mol, per mol of the compound of the present invention.

The method for synthesizing a β-ketoanilide compound from an acetyl compound and an isocyanate compound is known, and the method shown below is a typical known process.

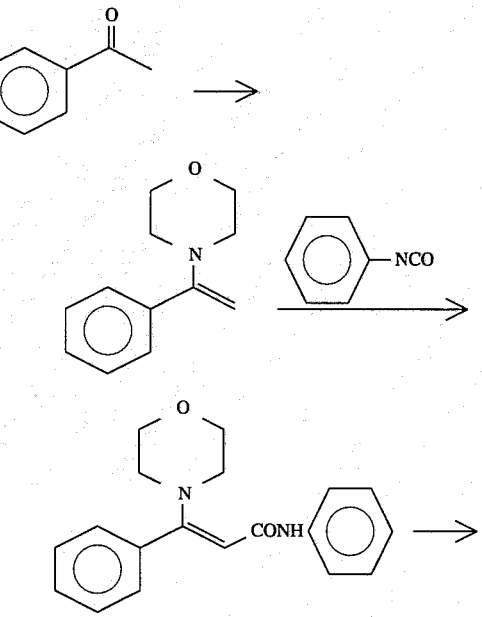

Chem. Ber., 95, 926 (1962)

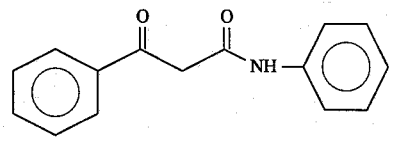

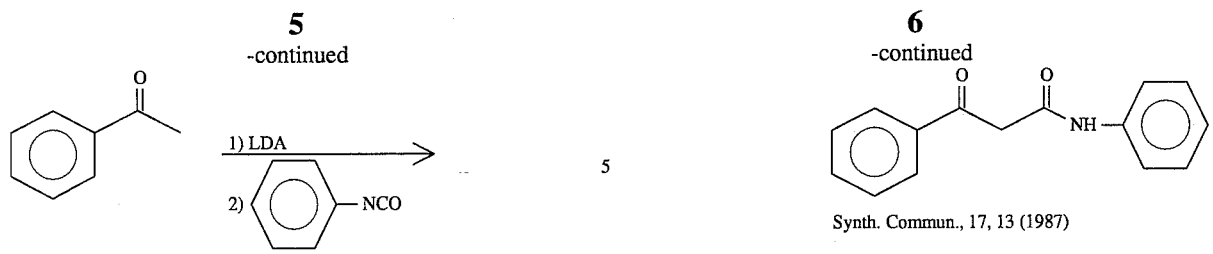

Synth. Commun., 17, 13 (1987)

Specific examples of the compound of the present invention are shown below, but the present invention is not limited to them.

TABLE 1

R¹COCH₂—[benzotriazole with (R²)n]

| Compound | R¹ | R² | n | Substituted position |
|---|---|---|---|---|
| (1) | $(t)C_4H_9-$ | $-CO_2-\text{Ph}$ | 1 | 5 |
| (2) | $(t)C_4H_9-$ | $-CO_2-\text{Ph}$ | 1 | 6 |
| (3) | $(t)C_4H_9-$ | —N=(N-methylbenzothiazol-2-ylidene) | 1 | 5 |
| (4) | $(t)C_4H_9-$ | —N=(N-methylbenzothiazol-2-ylidene) | 1 | 6 |
| (5) | $(t)C_4H_9-$ | $-NHCOC_9H_{19}$ | 1 | 5 |
| (6) | $(t)C_4H_9-$ | $-NHCOC_9H_{19}$ | 1 | 6 |
| (7) | $(t)C_4H_9-$ | Cl | 2 | 5, 6 |
| (8) | $C_{18}H_{37}O-\text{C}_6H_4-$ | $-NHCOC_7H_{15}$ | 1 | 5 |
| (9) | $C_{18}H_{37}O-\text{C}_6H_4-$ | $-NHCOC_7H_{15}$ | 1 | 6 |
| (10) | $C_{18}H_{37}O-\text{C}_6H_4-$ | —N=(N-methylbenzothiazol-2-ylidene) | 1 | 5 |
| (11) | $C_{18}H_{37}O-\text{C}_6H_4-$ | —N=(N-methylbenzothiazol-2-ylidene) | 1 | 6 |

TABLE 1-continued

R¹COCH₂—[benzotriazole with positions 1,2,3,4,5,6,7 and (R²)ₙ substituent]

| Compound | R¹ | R² | n | Substituted position |
|---|---|---|---|---|
| (12) | C₁₆H₃₃O—C₆H₄— | —CO₂CH₃ | 1 | 5 |
| (13) | C₁₆H₃₃O—C₆H₄— | —CO₂CH₃ | 1 | 6 |
| (14) | CH₃O—C₆H₄— | — | 0 | — |
| (15) | indoline-N— | —CO₂—C₆H₅ | 1 | 5 |
| (16) | indoline-N— | —CO₂—C₆H₅ | 1 | 6 |
| (17) | indoline-N— | —CO₂CH₂CO₂CH₂CH₂CH(CH₃)₂ | 1 | 5 |
| (18) | indoline-N— | —CO₂CH₂CO₂CH₂CH₂CH(CH₃)₂ | 1 | 6 |
| (19) | indoline-N— | —NHCOC₅H₁₁ | 1 | 5 |
| (20) | indoline-N— | —NHCOC₅H₁₁ | 1 | 6 |

TABLE 1-continued

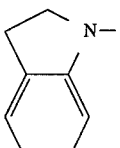

| Compound | R¹ | R² | n | Substituted position |
|---|---|---|---|---|
| (21) | 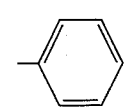 | — | 0 | — |
| (22) | (t)C$_4$H$_9$— | Cl | 2 | 4, 7 |
| (23) | (t)C$_4$H$_9$— | —OCH$_3$ | 2 | 4, 7 |
| (24) | (t)C$_4$H$_9$— | Cl | 1 | 4 |
| (25) | (t)C$_4$H$_9$— | Cl | 1 | 7 |
| (26) | (t)C$_4$H$_9$— | —OCH$_3$ | 1 | 4 |
| (27) | (t)C$_4$H$_9$— | —OCH$_3$ | 1 | 7 |
| (28) | (t)C$_4$H$_9$— | —CN | 1 | 4 |
| (29) | (t)C$_4$H$_9$— | —CN | 1 | 7 |
| (30) | (t)C$_4$H$_9$— | —NHCOC$_5$H$_{11}$ | 1 | 4 |
| (31) | (t)C$_4$H$_9$— | —NHCOC$_5$H$_{11}$ | 1 | 7 |
| (32) | (t)C$_4$H$_9$— | —CH$_3$ | 2 | 5, 6 |
| (33) | (t)C$_4$H$_9$— | —NHSO$_2$C$_4$H$_9$ | 1 | 4 |
| (34) | (t)C$_4$H$_9$— | —NHSO$_2$C$_4$H$_9$ | 1 | 7 |
| (35) | (t)C$_4$H$_9$— | 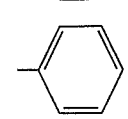 | 1 | 5 |
| (36) | (t)C$_4$H$_9$— | 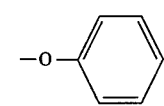 | 1 | 6 |
| (37) | (t)C$_4$H$_9$— | Br | 2 | 5, 6 |
| (38) | (t)C$_4$H$_9$— | —NO$_2$ | 1 | 5 |
| (39) | (t)C$_4$H$_9$— | —NO$_2$ | 1 | 6 |
| (40) | (t)C$_4$H$_9$— | —NO$_2$ | 1 | 4 |
| (41) | (t)C$_4$H$_9$— | —NO$_2$ | 1 | 7 |
| (42) | (t)C$_4$H$_9$— | 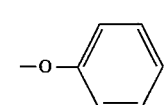 | 1 | 5 |
| (43) | (t)C$_4$H$_9$— | 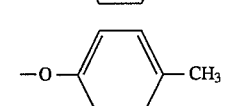 | 1 | 6 |
| (44) | (t)C$_4$H$_9$— | 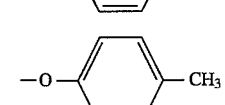 | 1 | 4 |
| (45) | (t)C$_4$H$_9$— | 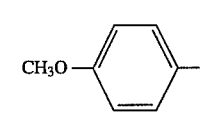 | 1 | 7 |
| (46) | CH$_3$O—⟨⟩— | —NO$_2$ | 2 | 4, 7 |

TABLE 1-continued

R¹COCH₂—(benzotriazole with positions 1,2,3,4,5,6,7)—(R²)ₙ

| Compound | R¹ | R² | n | Substituted position |
|---|---|---|---|---|
| (47) | CH₃O—C₆H₄— | —NO₂ | 1 | 5 |
| (48) | CH₃O—C₆H₄— | —NO₂ | 1 | 6 |
| (49) | CH₃O—C₆H₄— | —NO₂ | 2 | 5, 6 |
| (50) | C₈H₁₇O—C₆H₄— | —CN | 1 | 4 |
| (51) | C₆H₁₃O—C₆H₄— | —CN | 2 | 4, 7 |
| (52) | C₆H₁₃O—C₆H₄— | —CN | 2 | 5, 6 |
| (53) | C₈H₁₇O—C₆H₄— | —CN | 1 | 7 |
| (54) | C₄H₉O—C₆H₄— | Cl | 2 | 5, 6 |
| (55) | C₂H₅O—C₆H₄— | Cl | 2 | 4, 7 |
| (56) | C₆H₁₃O—C₆H₄— | —OCH₃ | 2 | 5, 6 |
| (57) | C₁₀H₂₁O—C₆H₄— | —OCH₃ | 2 | 4, 7 |
| (58) | CH₃O—C₆H₄— | —NHCOCH₃ | 2 | 5, 6 |
| (59) | CH₃O—C₆H₄— | —NHCOC₃H₇ | 1 | 4 |

TABLE 1-continued

R¹COCH₂–[benzotriazole with (R²)ₙ]

| Compound | R¹ | R² | n | Substituted position |
|---|---|---|---|---|
| (60) | 4-CH₃O-C₆H₄– | –NHCOC₃H₇ | 1 | 7 |
| (61) | 4-CH₃O-C₆H₄– | –NHSO₂C₄H₉ | 2 | 5, 6 |
| (62) | indolin-1-yl | Cl | 2 | 5, 6 |
| (63) | indolin-1-yl | –CH₃ | 2 | 5, 6 |
| (64) | indolin-1-yl | –OCH₃ | 2 | 4, 7 |
| (65) | indolin-1-yl | –NHCOCH₃ | 1 | 4 |
| (66) | indolin-1-yl | –NHCOCH₃ | 1 | 7 |
| (67) | indolin-1-yl | –CN | 2 | 5, 6 |

TABLE 1-continued

| Compound | R¹ | R² | n | Substituted position |
|---|---|---|---|---|
| (68) | (indoline-N-CH₂CH₂-) | —OCH₃ | 2 | 5, 7 |
| (69) | (indoline-N-CH₂CH₂-) | —OCH₃ | 2 | 4, 6 |

The compound of the present invention may be used as a synthesis intermediate from which a yellow coupler can be synthesized in a simple manner. Using the compound of the present invention, a yellow coupler can be readily produced on an industrial scale with the short process.

Now the present invention will be described in detail with reference to the following Examples and Reference Example, but the present invention is not limited to them.

EXAMPLE 1 (SYNTHESIS OF COMPOUNDS (1) AND (2))

4.78 g (0.02 mol) of 5-phenoxycarbonylbenzotriazole and 3.0 g (0.022 mol) of chloropinacolone were dissolved in 50 ml of acetonitrile, and then 3.1 ml of triethylamine was added to the solution, followed by heating under reflux for 2 hours. The temperature of the reaciton mixture was brought to room temperature; ethyl acetate and water were added to the reaction mixture; the ethyl acetate layer was separated and was washed with water; the solvent was distilled off, and crystallization with an n-hexane/ethyl acetate system was carried out, to obtain 6.20 g of mixed crystals of (1) and (2). Yield: 92%. Melting point: 157°–174° C.

Compound (1) (or (2))
  ¹H-NMR (CDCl₃: 200 MHz)
  δppm 1.40 (s, 9 H)
  5.70 (s, 2 H)
  7.20–7.53 (m, 6 H)
  8.20–8.38 (m, 2 H)
Compound (2) (or (1))
  ¹H-NMR (CDCl₃: 200 MHz)
  δppm 1.40 (s, 9 H)
  5.74 (s, 2 H)
  7.20–7.53 (m, 6 H)
  8.20–8.38 (m, 2 H)

Based on the volume ratio of ¹H-NMR, it could be said that the mixture was an about 1:1 mixture of Compound (1) and Compound (2).

EXAMPLE 2 (SYNTHESIS OF COMPOUND (14))

Conditions almost similar to those in Example 1 were used for the synthesis.

Melting point: 128°–132° C.
¹H-NMR (CDCl₃: 200 MHz)
δppm 3.92 (s, 3 H)
6.07 (s, 2 H)
7.02 (d, 2 H, J=8.7 Hz)
7.35–7.52 (m, 3 H)
8.06 (d, 2 H, J=8.7 Hz)
8.0–8.15 (m, 1 H)

EXAMPLE 3 (SYNTHESIS OF COMPOUNDS (17) AND (18))

The synthesis was carried out almost in the same way as in Example 1, thereby obtaining mixed crystals of (17) and (18). Based on the volume ratio of ¹H-NMR, it could be said that the mixture was an about 1:0.9 (the ratio of (17):(18)) mixture of (17) and (18).

Compound (17) (or (18))
  Melting point: 120°–124° C.
  ¹H-NMR-(CDCl₃: 300 MHz)
  δppm 0.88 (s, 6 H)
  1.50–1.80 (m, 3 H)
  3.31 (t, 2 H, J=8.0 Hz)
  4.14–4.34 (m, 4 H)
  4.86 (s, 2 H)
  5.62 (s, 2 H)
  7.01–7.33 (m, 4 H)
  7.67 (d, 1 H, J=9.0 Hz)
  8.26 (d, 1 H, J=9.0 Hz)
  8.43 (s, 1 H)

EXAMPLE 4 (COMPOUND (21))

Melting point: 230°–232° C.
¹H-NMR (CDCl₃: 300 MHz)

δppm 3.30 (t, 2 H, J=9.0 Hz)
4.23 (t, 2 H, J=9.0 Hz)
5.58 (s, 2 H)
7.05 (t, 1 H, J=7.0 Hz)
7.17 (t, 1 H, J=8.0 Hz)
7.21 (d, 1 H, J=8.0 Hz)
7.38 (t, 1 H, J=8.0 Hz)
7.50 (t, 1 H, J=8.0 Hz)
7.62 (d, 1 H, J=8.0 Hz)
8.09 (d, 1 H, J=8.0 Hz)
8.12 (d, 1 H, J=8.0 Hz)

The synthesis of yellow couplers obtained by using the compound of the present invention will be described.

Typical yellow couplers that can be derived from the compound of the present invention are shown below. These are known to be useful as DIR yellow couplers described, for example, in U.S. Pat. Nos. 4,095,984, 4,477,563, and 5,213,958.

TABLE 2

| Compound of the present invention | Yellow coupler | |
|---|---|---|
| (1), (2) | (Y-1) (Y-2) | 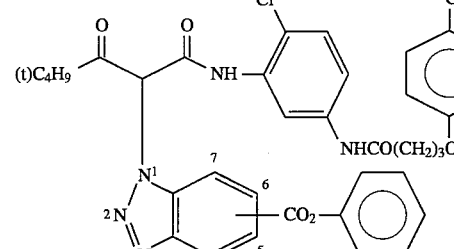 Substituted position; 5- or 6-position |
| (3), (4) | (Y-3) (Y-4) | 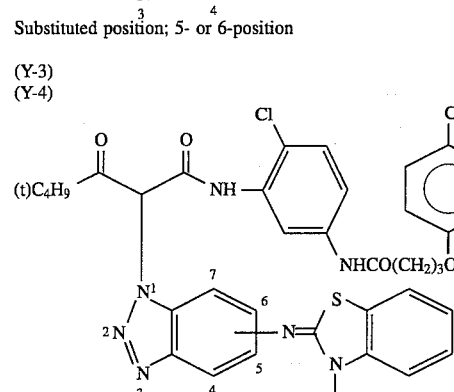 Substituted position; 5- or 6-position |
| (8), (9) | (Y-5) (Y-6) | 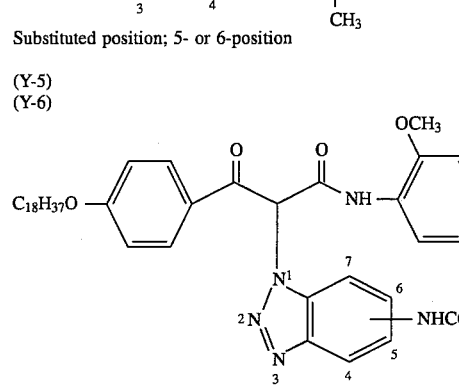 Substituted position; 5- or 6-position |
| (10), (11) | (Y-7) (Y-8) | |

TABLE 2-continued

| Compound of the present invention | Yellow coupler |
|---|---|
| (17), (18) | (Y-9) (Y-10) |

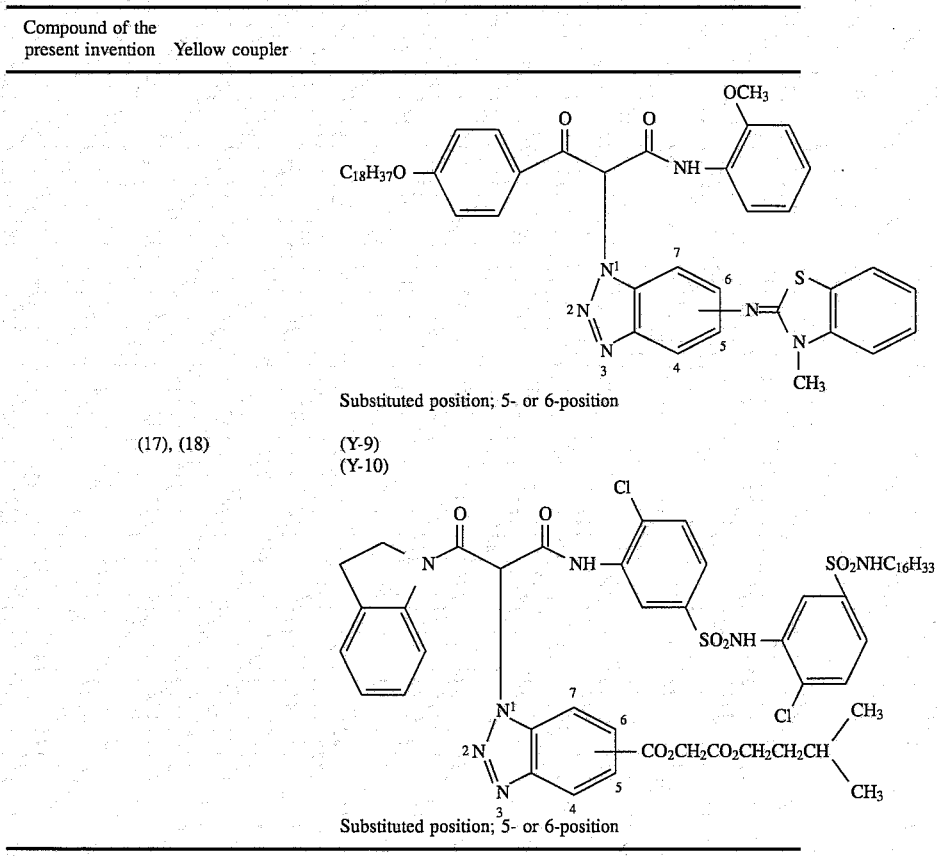

Substituted position; 5- or 6-position

The melting points of typical yellow couplers (mixtures) are shown below:

(Y-3) and (Y-4): 130°–136° C.
(Y-5) and (Y-6): 163°–166° C.
(Y-7) and (Y-8): 140°–142° C.

Reference Example 1

(Synthetic Example of Yellow Couplers (Y-9) and (Y-10) Using Compounds (17) and (18) of the Present Invention)

0.46 g (11.5 mmol) of sodium hydride (60%) was dispersed in 20 ml of N,N-dimethylformamide, and then 1.18 g (3 mmol) of the mixture of (17) and (18) and 2.20 g (3 mmol) of N-[2-chloro-5-(2-chloro-5-hexadecylsulfamoylphenylsulfamoyl)phenyl]phenoxycarbonamide were added to the dispersion, followed by stirring at room temperature for 3 hours. The reaction mixture was poured into ice water containing 1.5 ml of hydrochloric acid, and the deposited crystals were filtered off. The crystals were purified by column chromatography (methylene chloride/ethyl acetate=from 10/1 to 5/1), to obtain 2.35 g of a mixture of yellow couplers (Y-9) and (Y-10). Yield: 78%.

Having described our invention as related to the present embodiments, it is our intention that the invention not be limited by any of the details of the description, unless otherwise specified, but rather be construed broadly within its spirit and scope as set out in the accompanying claims.

What we claim is:

1. A compound represented by formula (I):

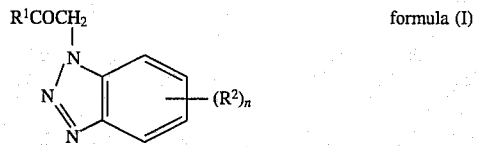

formula (I)

wherein $R^1$ represents an indoline-1-yl group; $R^2$ represents a group selected from the group consisting of a halogen atom, a cyano group, a nitro group, an alkoxy group having 1 to 20 carbon atoms, an alkyl group having 1 to 20 carbon atoms, an aryl group having 6 to 20 carbon atoms, an aryloxy group having 6 to 20 carbon atoms, an aryloxycarbonyl group having 7 to 20 carbon atoms, an acylamino group having 1 to 20 carbon atoms, a sulfonamide group having 1 to 20 carbon atoms, a group of the formula $-CO_2R^6$, wherein $R^6$ represents an aryl group having 6 to 20 carbon atoms or an alkyl group having 1 to 20 carbon atoms, and a group represented by the formula (II):

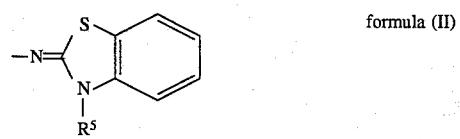

formula (II)

wherein $R^5$ represents an alkyl group having 1 to 20 carbon atoms; and n is an integer of 0 to 4.

2. The compound as claimed in claim 1, wherein $R^2$ is an acylamino group having 1 to 8 carbon atoms, a group represented by formula (II), or a group represented by $-CO_2R^6$:

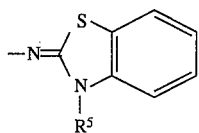

wherein $R^5$ represents an alkyl group having 1 to 20 carbon atoms, and $R^6$ represents an aryl group having 6 to 20 carbon atoms, or an alkyl group having 1 to 20 carbon atoms.

3. The compound as claimed in claim 1, wherein $R^2$ is an acylamino group having 1 to 8 carbon atoms, a group represented by formula (II), or a group represented by —$CO_2R^6$:

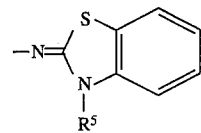

wherein $R^5$ represents a methyl group, and $R^6$ represents a phenyl group or a 3-methylbutoxycarbonylmethyl group.

4. The compound as claimed in claim 1, wherein n is 0, 1, or 2.

5. The compound as claimed in claim 1, wherein $R^2$ is an acylamino group having 1 to 8 carbon atoms and n is 1.

6. The compound as claimed in claim 1, wherein $R^2$ is a group represented by the formula —$CO_2R^6$ and n is 1.

* * * * *